(12) United States Patent
Gwon et al.

(10) Patent No.: US 6,322,556 B1
(45) Date of Patent: Nov. 27, 2001

(54) METHOD OF LASER PHOTOABLATION OF LENTICULAR TISSUE FOR THE CORRECTION OF VISION PROBLEMS

(75) Inventors: Arlene E. Gwon, 8 Trafalgar, Newport Beach, CA (US) 92660; Michael W. Berns, Trabuco Canyon, CA (US)

(73) Assignee: Arlene E. Gwon, Newport Beach, CA (US)

( * ) Notice: Subject to any disclaimer, the term of this patent is extended or adjusted under 35 U.S.C. 154(b) by 0 days.

(21) Appl. No.: 08/103,089

(22) Filed: Aug. 6, 1993

Related U.S. Application Data

(63) Continuation-in-part of application No. 07/785,140, filed on Oct. 30, 1991, now abandoned.

(51) Int. Cl.$^7$ ..................................................... A61F 9/008
(52) U.S. Cl. ..................................... 606/6; 606/3; 606/13
(58) Field of Search ............................................ 606/2–19

(56) References Cited

U.S. PATENT DOCUMENTS 4,309,998 * 1/1982 Aron nee Rosa et al. ............... 606/6
4,538,608 * 9/1985 L'Esperance, Jr. ..................... 606/10
4,907,586 * 3/1990 Bille et al. ................................ 606/5

* cited by examiner

Primary Examiner—David M. Shay
(74) Attorney, Agent, or Firm—Walter A. Hackler

(57) ABSTRACT

A method for the laser photoablation of ocular lens tissue comprises the steps of determining a volume of the lens tissue to be photoablated and directing a pulsed, infrared laser beam at the volume with an amount of energy effective for photoablating the determined region without causing substantial damage to surrounding tissue regions. The laser beam is initially directed at a focal point below an anterior surface of the ocular lens and such focal point is moved towards the ocular lens anterior surface in order to ablate the determined volume. The laser is preferably an Nd:YLF laser operating at a frequency of about 1053 nanometers and a pulse repetition rate of about 1000 Hertz with a pulse width of about 60 picoseconds. Each pulse has an energy of about 30 microjoules. The laser operates with a focused beam diameter of about 20 microns and operates with a "zone of effect" of no greater than about 50 microns. The method provides for the correction of myopia, hyperopia or presbyopia and enables the removal of incipient cataract.

26 Claims, 2 Drawing Sheets

METHOD OF LASER PHOTOABLATION OF LENTICULAR TISSUE FOR THE CORRECTION OF VISION PROBLEMS

The present application is a continuation-in-part of U.S. Ser. No. 07/785,140, filed Oct. 30, 1991 now abandoned.

BACKGROUND OF THE INVENTION

1. Field of the Invention

The present invention relates generally to the field of photoablation of ocular tissue to correct vision deficiencies and treat other vision-impairing ocular problems and, more particularly, to treatment of the natural ocular lens.

2. Background Discussion

Historically, and until only a few decades ago, eyeglasses (i.e., spectacles) were exclusively used for most correctable vision deficiencies, including, for example, hyperopia (wherein incident parallel rays of light converge to focus behind the retina), myopia (wherein incident parallel rays of light converge to a focus in front of the retina), and astigmatism (a defect in vision ordinarily caused by irregularities in the cornea). However, in about the 1940s, contact lens started being used as a viable alternative, at least for many individuals, to the use of spectacles for correcting vision deficiencies, and provided—often at a cost of some discomfort—freedom from many annoyances and appearance problems associated with the wearing of spectacles.

Another method for treating some types of problems causing vision problems was introduced by Dr. Peter Ridley just after the close of World War II. This new (although there is some evidence that it had been tried several hundred years ago) method involved the replacement of a diseased natural ocular lens, for example, a natural lens which had been clouded because of cataract, with a plastic artificial or prosthetic intraocular lens (IOL). Such lens extraction and IOL implantation is now a commonly-performed surgical procedure and is credited with saving the sight of many individuals who were or would have become blind.

Vision correction can now be achieved on some patients, especially those with myopia, by a surgical procedure on the cornea called radial keratotomy (RK). In an RK procedure, several slits (for example, about four to about eight) are made radially inwardly toward the optical axis from the peripheral edge of the cornea. These radial slits enable the cornea to flatten out a bit, thereby decreasing the curvature of the cornea. Candidates for RK procedures are typically nearsighted individuals who cannot or who do not want to wear either spectacles or contact lenses.

Corneal onlays or implants, which may be constructed of synthetic materials or from donor corneas, which are surgically attached to or implanted into patients'eyes, are also useful to enhance vision in patients whose corneas have been damaged and/or scarred by corneal diseases, such as ulcers or cancer, or by injury to the cornea.

Because of the shortcomings associated with RK surgery and a desire to provide vision correction to many individuals without the necessity for those individuals to wear spectacles or contact lenses, considerable research and development have been directed over the past several years to apparatus and techniques for reshaping the anterior (forward) surface of the cornea.

Excimer lasers—lasers operating in the ultraviolet (UV) region of less than about 200 nanometers wavelength—have thus now been used to selectively ablate regions of the cornea to resculpture the corneas of patients in a manner correcting certain vision problems. For example, regions of the cornea around its optical axis are photoablated to a greater depth than peripheral regions of the cornea, thereby decreasing the curvature of the cornea to correct myopia.

In contrast, photoablation of the cornea is concentrated near the periphery of the cornea to increase the curvature of the cornea and thereby correct for hyperopia. In a related manner, astigmatism can be corrected by selectively varying the rate of laser photoablation of an astigmatic cornea in a manner providing an appropriate vision correction. In this regard, U.S. Pat. No. 4,784,135 to Blum et al. discloses a method for removing biological tissue by irradiation of the tissue with UV radiation while, for example, U.S. Pat. Nos. 4,665,913; 4,669,466; 4,718,418; 4,721,379; 4,729,372; 4,732,149; 4,770,172; 4,773,414; and 4,798,204 to L' Esperance disclose apparatus and methods for laser sculpting of corneal tissue to correct vision defects.

In addition, U.S. Pat. No. 4,842,782 to Portney et al. and U.S. Pat. No. 4,856,513 to Muller (as well as one or more of the above-cited L' Esperance patents) disclose masks useful for selectively controlling the laser beam intensity or total laser beam energy to different regions to thereby enable selective corneal ablation to effect the desired vision correction. Various of the above-cited patents to L' Esperance also disclose methods for determining the required laser ablation profile for the cornea. For example, U.S. Pat. No. 4,995,923 discloses computer mapping of the cornea and computer-controlled scanning of the cornea by the laser beam.

In spite of reported short-term medical successes—both in clinical testing in the United States and in use in unregulated foreign countries—with laser photoablation of corneal tissue to correct vision deficiencies, the verdict is still not in concerning the long-term effects and efficacy of corneal laser photoablation.

In particular, questions have been raised whether over a long term the vision correction initially provided by photoablation of the cornea will remain effective because of the normal regrowth of the removed epithelium layer of the cornea over the ablated area. In this regard, there seems to be at least some natural tendency for the epithelium layer to regrow in a manner that, in time, the pre-ablation contour of the cornea may be reestablished sufficiently so that vision recorrection is required. An ancillary question is, therefore, how many times and how frequently can a laser photoablation process be repeated?

Also, there have been reports of haze forming on the cornea after photoablation. Although this appears to be a relatively transient phenomenon—lasting only a few months and ordinarily not too bothersome to the patient—at the present there has been insufficient post-ablation time on any patients to determine long term effects.

Moreover, it appears that there may be a maximum diopter change—around five diopters—that can presently be effectively and predictably made by corneal photoablation. Still further, at least at present, the laser ablation of corneal tissue is extremely painful to the patient on which the surgical procedure is performed.

Further, with respect to laser photoablation of the cornea, it should be appreciated that although in so doing, the cornea is sculpted in a manner correcting vision, it is frequently the case that the cornea itself is not responsible for the vision problems being corrected. As an illustration, myopia may more likely be caused by an increase in lens size, usually as a natural effect of the human aging process, of the natural lens of the eye (located posteriorly of the cornea). Other vision defects or deficiencies may also originate at the natural lens, while the associated cornea may itself be in a normal condition.

For these and other reasons, and for the reason that because the lens is closer to the retina than is the cornea, less material would have to be removed from the lens to achieve a similar vision correction, the present inventor has determined that it would often be preferable to reprofile the natural lens over reprofiling the cornea. Such natural lens reprofiling would eliminate many of the concerns presently raised about corneal photoablation and may result in reduced risks to patients; and since the lens has no nerve supply, the procedure should result in no sensation of pain to the patient.

It is therefore, a principal objective of the present invention to provide a method for laser ablation of selected regions of the natural lens in order to correct vision problems and to correct problems, such as incipient cataract, on the lens.

SUMMARY OF THE INVENTION

According to the present invention, there is provided a method for the laser photoablation of ocular lens tissue, the method comprising the steps of determining the volume of the lens tissue to be photoablated and directing a pulsed laser beam at such volume with an amount of energy effective for photoablating the region without causing substantial damage to the surrounding tissue regions.

The laser is initially directed, or focused, at a focal point below an anterior surface of the ocular lens and such focal point is moved toward the ocular lens anterior surface in order to ablate the determined volume. As also described herein, an alternative embodiment of the present invention includes the initiation of photoablation of the surface of the the ocular lens anterior surface and thereafter moving the focal point inwardly and away from the anterior surface in order to promote the absorption of laser by products by adjacent healthy tissue.

It also may be preferable to photoablate a plurality of cube-like volumes in said ocular lens. In this regard, a laser suitable for use in the present invention may be an Nd:YLF laser having an operating frequency in the infrared spectrum and more preferably having an operating frequency of about 1053 nanometers. The laser preferably has a repetition rate of between about 1 and about 1000 Hertz, and more preferably about 1000 Hertz, and operates with a pulse width of between about 1 femtosecond and about 1 millisecond and, more preferably, about 60 picoseconds.

Moreover, the laser preferably may operate at an energy level of between about 1 nanojoule and about 50 millijoules per pulse and, more preferably, about 30 microjoules. Still further, the laser preferably operates with a beam spot diameter of between about 1 micron and about 100 microns and, more preferably, with a beam spot diameter of about 20 microns.

The laser preferably operates with a zone of effect of less than about 200 microns and, more preferably, with a zone of effect of less than about 50 microns.

In accordance with one embodiment of the invention, a method is provided for the laser photoablation of ocular lens tissue for the correction of myopia, hyperopia, or presbyopia. In this case, the method comprises the steps of determining the region of the lens tissue to be photoablated, calculating the amount of lens tissue to be photoablated from the determined region, and directing the pulsed infrared laser beam at the region with an amount of energy effective for photoablating the calculated amount of lens tissue in the determined region without causing substantial damage to lens tissue surrounding such region.

In another embodiment of the invention, a method is provided for the laser photoablation of ocular lens tissue for the removal of incipient cataract, the method comprising the steps of determining the region of the lens tissue to be photoablated so as to remove the incipient cataract, calculating the amount of lens tissue to be photoablated from the determined region so as to remove the incipient cataract; and directing the pulsed infrared laser beam at the region with an amount of energy effective for photoablating the calculated amount of lens tissue in the determined region so as to remove the incipient cataract without causing substantial damage to lens tissue surrounding such region.

BRIEF DESCRIPTION OF THE DRAWINGS

The present invention can be more readily understood by a consideration of the following detailed description when taken in conjunction with the accompanying drawings in which:

FIG. 3a showing the manner in which internal regions of the lens are photoablated for the purpose of correcting myopia, hyperopia or presbyopia; and FIG. 3b showing the manner in which generally surface and subsurface regions of the lens are photoablated to remove incipient cataract.

In the various figures, identical elements and features are given the same reference number.

DETAILED DESCRIPTION OF THE INVENTION

Figure 1:
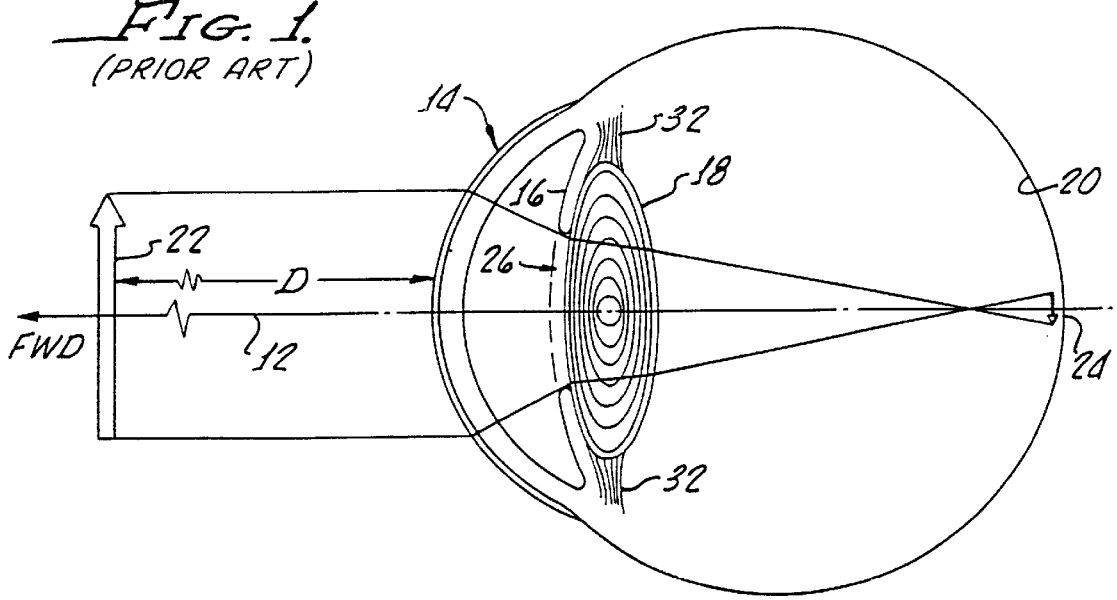
FIG. 1 is a longitudinal cross sectional drawing of a representative eye showing, in simplified form, the cornea, iris, natural lens and retina, and showing the manner in which an image is focused on the retina in a normal eye.

There is shown in FIG. 1, in greatly simplified diagrammatic form, a longitudinal cross sectional drawing of a typical normal eye, which is generally symmetrical about an optical axis 12. Shown comprising the eye and in order from the front of the eye to the back are a cornea 14, an iris 16, a natural lens 18 and a retina 20. In a normal eye, light from an object 22 is refracted by cornea 14 and lens 18 so as to form an image 24 on retina 20 (iris 16 being shown as having an open central aperture 26 permitting light to pass through to the lens).

Figure 2:
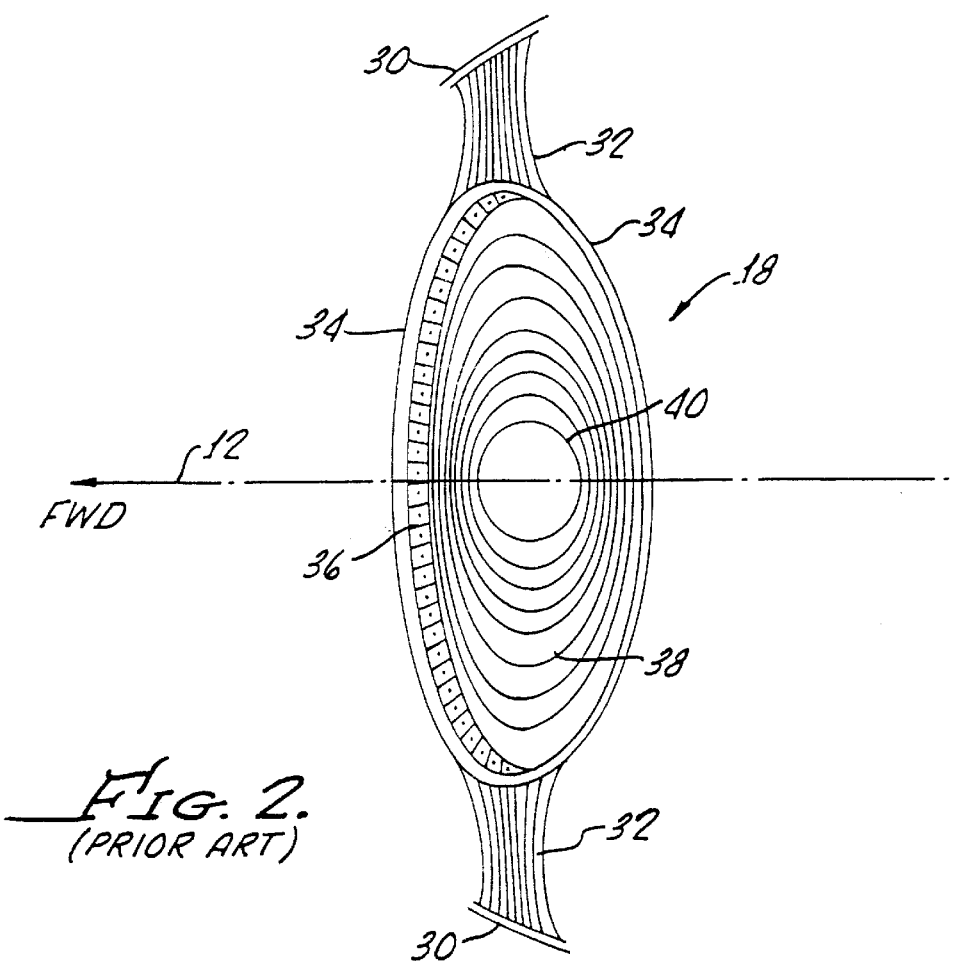
FIG. 2 is an enlarged, longitudinal cross sectional drawing of a normal lens showing, in simplified form, its composition.

Shown more particularly in FIG. 2 (but still in greatly simplified form), lens 18 is a biconvex, somewhat flexible structure which is suspended behind iris 16 and is connected to a peripheral ciliary body 30 of the eye by zonal fibers (zonules) 32. Since lens 18 is avascular, its pathology is more simple than most other tissues of the body; primary inflammation processes do not occur and neoplastic growths in lens 18 are unknown. However, trauma or injury to lens 18 results in passive and degenerative changes in the lens with consequent opacification.

Focusing of lens 18, which functions to transmit and refract light to retina 20, is (assuming the lens is in its normal, youthful condition) by contraction and relaxation of zonal fibers 32. In the relaxed state of fibers 32, lens 18 assumes its maximum convex curvature and thickness; as tension in zonal fibers increases, lens 18 is stretched and its convex curvature and thickness are decreased. By this mechanism, called accommodation, the shape of lens 18 is physically varied in a manner causing images 22 to be correctly focused on retina 20 as the distance D between object 22 and cornea 14 changes between far and near. (See FIG. 1.)

Lens 18 consists of about 65% water and about 35% protein (known as crystallins), along with traces of minerals. Lens 18 is avascular, containing no blood vessels, and has no nerve supply, and comprises a thin, transparent capsule or bag 34, a subcapsular epithelium layer 36, a cortex 38 of soft fibers and a harder, dense nucleus 40 at the center. During development of lens 18, surface ectoderm invaginates to form the lens vesicle.

The posterior cells of the lens vesicle then elongate to form the primary lens fibers, which obliterate the cavity of the vesicle and abut on the anterior (forward) epithelium layer 36. This process is completed early in fetal development. Subsequently, secondary lens fibers are added throughout life by the elongation and differentiation of epithelial cells circumferentially at the equator of lens 18. The net result is the progressive internalization of previously-formed fibers. The older fibers are always found toward nucleus 40 and the younger fibers toward cortex 38.

Lens 18 continues to grow throughout an individual's life in a process similar to that in which the epidermal tissue of the skin renews itself. However, unlike the skin where old cells are continually cast off from the surface, older lens cells accumulate centrally and cannot be cast off. The net result is progressive growth of lens 18 with age, associated with a decrease in elasticity and accommodative ability. The result is that the most common degenerative condition of lens 18 is presbyopia, a condition in which loss of elasticity of the lens results in the inability of the eye to focus sharply for near vision, such that most individuals by about the age of forty require some visual assistance, for example, that provided by spectacles, contact lenses or RK surgery.

Another common degenerative condition of lens 18 that is generally associated with aging is cataract, which is generally defined as any opacity in the lens. In the case of cataract, the extent of disability depends upon the location and severity of the opacity.

Thus, a relatively small posterior (i.e., rearward) subcapsular cataract may be visually incapacitating because it is situated near the nodal point of the dioptric system, while peripheral opacities that do not impinge on optical axis 12 may cause little visual inconvenience. In general, patients initially complain of a visual disturbance, then a diminution of vision, and finally a complete failure of vision. For small lens opacities and early disturbance or diminution of vision, there is no proven therapeutic modality (i.e., treatment). Ophthalmologists have long considered removal of lens 18 as the only treatment for cataract.

At present, the most commonly performed operation is an extracapsular cataract extraction with intraocular lens implantation, the objective of the surgical procedure being to remove as much of the lens as possible with subsequent optical device correction. The concept of selective removal of a small opacity or sections of the lens was not heretofore considered nor would it have been technically possible.

Figure 3B:
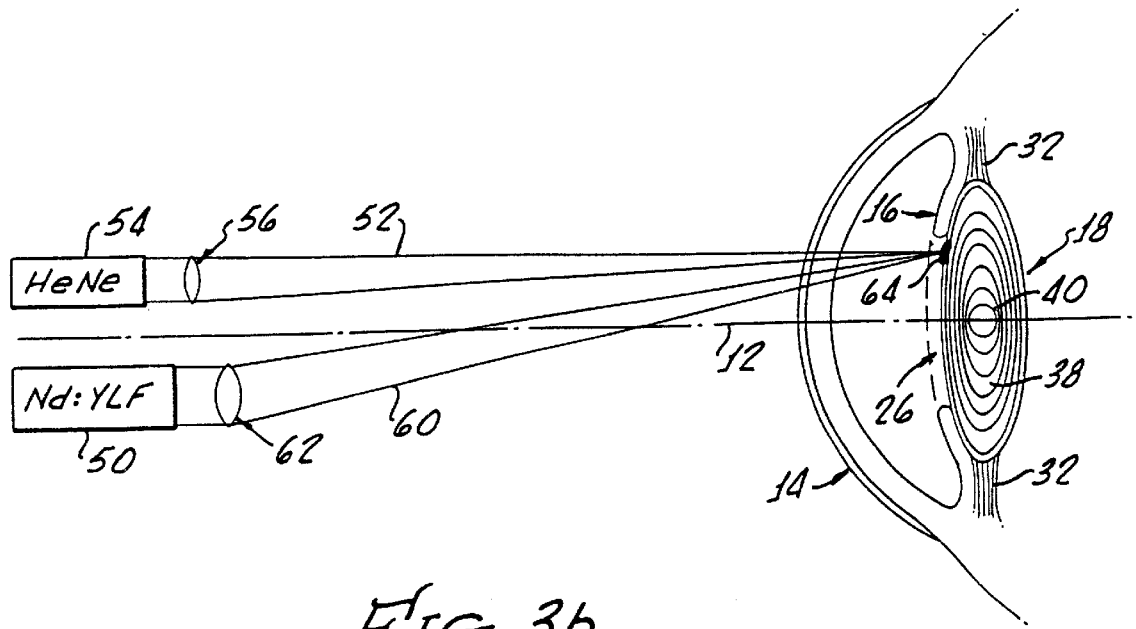
FIGS. 3a and 3b are simplified, longitudinal cross sectional drawing—similar to FIG. 1—showing the manner in which the natural lens has regions thereof photoablated using, for example, an Nd:YLF laser operating at a frequency of about 1053 nanometers and operating at a repetition rate of about 1000 pulses per second.
Figure 3A:
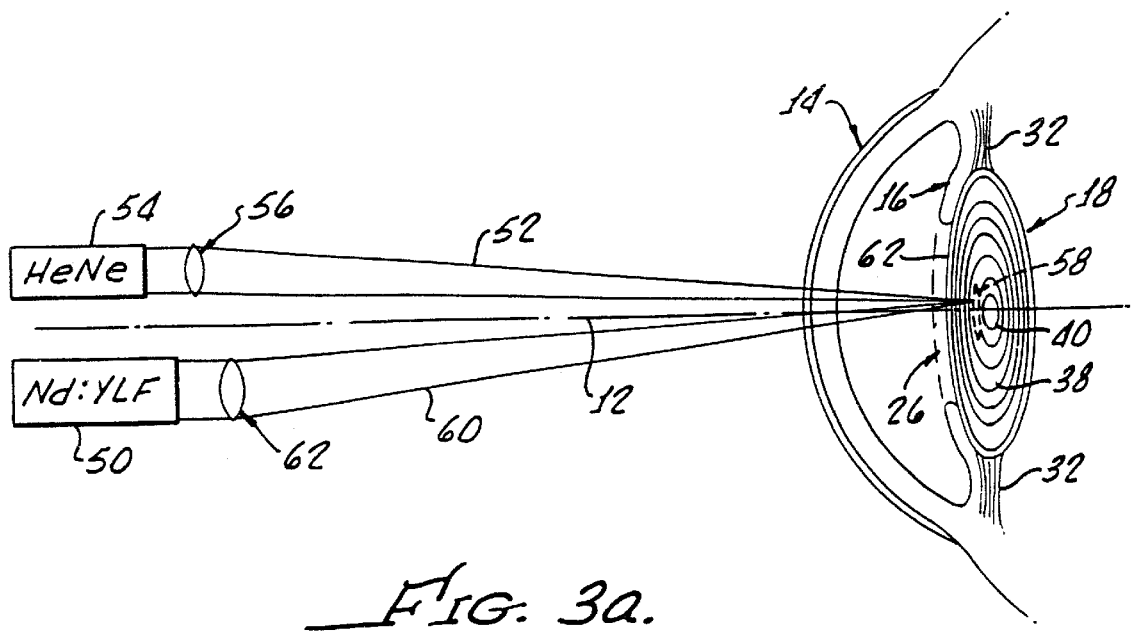

The present invention relates to methods to treat presbyopia, refractive errors, and cataract by means of focusing high power pulse laser photoablation of lens opacities and selected normal lens fibers. A laser 50 (FIG. 3a and 3b) which can advantageously be used for such purpose is preferably, but is not limited to, a quasi-continuous Nd:YLF picosecond laser which may be purchased as ISL Model 2001 MPL or 4001 CLS from Intelligent Laser Systems, Inc. of San Diego, Calif. In general, laser 50 produces a shock wave in the tissue at which its beam is focused, the shock wave expanding radially from the point of focus and disintegrating the target tissue (optical break-down), thereby causing ionization of the medium and the formation of a plasma.

This plasma is a gaseous state, formed when electrons are stripped away from their atoms in either a gas, liquid or solid. Once optical breakdown occurs, the plasma that is formed absorbs or scatters subsequent light in the laser pulse, thereby acting as an effective shield protecting underlying structures. The quicker the laser pulses, the faster and more easily the plasma is created.

For the present photoablation procedure, laser 50 preferably has the following characteristics:

(1) An operating frequency preferably in the visible and infrared (IR) spectrum; more preferably, about 1053 nanometers (nm);

(2) A repetition rate preferably ranging from about one to about 1000 Hertz; more preferably, about 1000 pulses per second;

(3) A pulse width preferably ranging from about 1 femtosecond to about 1 millisecond; more preferably, about 60 picoseconds;

(4) An energy level per pulse preferably ranging from about 1 nanojoule to about 50 millijoules; more preferably, about 60–140 microjoules.

(5) A focused spot size (diameter) preferably between about 1 micron and about 100 microns; more preferably, about 20 microns.

(6) A "zone of effect" preferably limited to between about 1 and about 200 microns with little collateral effect; more preferably, the zone of effect is limited to about 50 microns.

The procedure described hereinbelow for the laser photoablation of lens tissue ordinarily requires an initial ocular examination of the prospective patient, including refractive status, slit lamp biomicroscopy, and the measurement of axial length of lens 18 by standard applanation A-scan ultrasonography. The accommodative amplitude of lens 18 may be measured by various techniques.

For example, Adler (Moses RA. "Accommodation" In: Moses RA, Hart, MA Jr. eds., *Adler's Physiology of the Eye*, St. Louis, Washington, D.C., Toronto: The C.V. Mosby Co., Chapter 11, 1987:291–310—which is incorporated herein by specific reference) recommends that a convex lens be moved along the optical axis in front of the patient's eye, away from the eye, until a target object at a convenient distance just begins to blur—it is then assumed that accommodation is relaxed.

The convex lens is then reduced (to a concave lens), or, alternatively, the target object is brought closer to the patient's eye until the target again starts to blur. The range between the "far" blur and the "near" blur or maximum plus (convex lens) to blur and maximum minus (concave lens) to blur is the range of accommodation in diopters.

For the treatment of presbyopia, the amount of lens thickness to be ablated can be calculated in two ways:

(1) Based upon Normative Charts of lens thickness and accommodative amplitude with age:

Using the ultrasound data on sagittal lens length with age by Rafferty (Rafferty, N. S., "Lens Morphology" In: Maisel, H., ed., *The Ocular Lens*. Marcel Dekker, Inc., New York and Basel. 1985:1–15, 52–60—which is incorporated hereinto by specific reference) and the accommodative amplitude at a given age, as shown, by way of example, in Duane's Table (Borish, Irvin M., "Accommodation," *Clinical Refraction*, The Professional Press, Inc., Chicago, 1975, 34d Ed., Vol. 1, p. 170—which is incorporated hereinto by specific reference), the amount of required lens tissue ablation is calculated by subtracting the desired accommodation amplitude from the patient's actual accommodation amplitude. By way of illustration, with no limitation being thereby intended or implied, a patient of age 60 has a lens thickness of 4.66 mm and an accommodation amplitude of 1.25 diopters. To increase the patient's accommodative amplitude to that of a person of age 30 who has a lens thickness of 4.15 mm and an accommodative amplitude of 7.5 diopters, about 0.51 mm (4.66 mm minus 4.15 mm) of lens tissue is preferably removed from the patient's lens. This would represent an increase of approximately 6.25 diopters (7.5 diopters minus 1.25 diopters) of accommodative amplitude. Since the maximal thickness change in the lens during accommodation is about 0.5 mm, this change should be sufficient to restore the presbyopic 60-year old patient to an accommodative state.

(2) Based on the patient's measured lens thickness and amplitude of accommodation:

The amount of lens tissue to be ablated is calculated based on the work of Koretz and Handelman (Koretz, J. F., Handelman, G. H., "Model of the accommodation mechanism in the human eye," *Vision Res.*, Vol. 22, 1982:917–927—which is incorporated hereinto by specific reference). A two-micron change in lens thickness corresponds to a 0.02 diopter change in accommodation. Thus, if a patient's amplitude of accommodation measures 1.25 diopters and it is desired to increase that to 5 diopters (a change of 3.75 diopters), the amount of decrease in lens thickness required would be approximately 375 microns.

For the treatment of hyperopia, the amount of lens tissue to be ablated is calculated as described above for presbyopia. This will increase the amplitude of accommodation of the patient's lens to allow the hyperope to move the focus of distant objects up to his or her retina 20.

For the treatment of myopia, the amount of lens tissue to be ablated can be calculated based on the refractive status of the eye and the measured lens thickness as set forth above in Paragraph (2).

Procedure:

For the treatment of presbyopia and hyperopia, a beam 52 from an HeNe focusing laser 54 (FIG. 3*a*)is focused, by an associated lens or lens system 56, through cornea 14 (which is transparent to the focusing beam) and iris opening 26, to a region 56 to be photoablated by Nd:YLF laser 50 for correction of the specific vision problem under treatment. In this regard, it is preferred that the more centrally located, older cortical and/or nuclear fibers be ablated since the width of nucleus 40 (FIG. 2) remains relatively constant with age, whereas that of cortex 38 increases.

Then, a laser beam 60 from Nd:YLF laser 50 is focused by an associated focusing lens or lens system 62 through cornea 14 (which is transparent to the laser beam) and iris opening 26, onto region 56 which is to be photoablated by the Nd:YLF laser beam. The amount of lens tissue to be ablated (i.e., decomposed) to achieve the desired vision correction is determined in the manner described above.

The optical zone (equatorial diameter) should be approximately equal to the diameter of nucleus 40 and the axial width (for example, about 510 microns). For treatment of myopia, it is preferred that region 56 be selected so that nucleus 40 and/or centrally located older fibers in cortex 38 are ablated using a smaller optical zone so as to decrease the curvature of an anterior (forward) surface 62 of lens 18.

Such laser ablation of lens 18 to correct myopia, presbyopia and hyperopia may be termed "photorefractive phacoplasty" or "phototherapeutic phacoplasty".

For the treatment of cataracts (FIG. 3*b*), beam 52 from HeNe focusing laser 54 (FIG. 3) may be directly focused by lens or lens system 56 (with the beam passing through cornea 14 and iris opening 26) onto an area or region 64 of small lenticular opacity. Then beam 60 from Nd:YLF laser 50 is focused, by lens or lens system 62 onto area or region 64 and the laser is pulsed until the opacity is ablated (as determined, for example, by visual observation through cornea 12 and iris opening 26).

It is preferred that if opacity area or region 64 is adjacent to lens capsule 18 (FIG. 2), aiming beam 52 from HeNe laser 52 is focused more centrally to the opacity to account for shock wave expansion. Such treatment (i.e., photoablative removal) of incipient cataract, which is intended to delay or prevent full cataract surgery, including removal of lens 18 and the replacement thereof with an IOL, may be termed phototherapeutic phacoablation" or "photo-therapeutic phacoectomy".

In either of the above-described treatments, application of photoablation beam 60 from Nd:YLF laser 50 produces the formation of gas bubbles (by-products) at the site of optical breakdown by the focused beam within lens 18 (that is, at regions such as above-described regions 58 and 64). The formed gas bubbles are, however, usually reabsorbed within lens 18 within 24 to 48 hours and lens 18 remains optically clear. Reabsorption may occur faster if the photoablation is effected adjacent healthy tissue. Thus, in one embodiment of the present invention, the method includes initiating photoablation at the surface of the ocular tissue and thereafter the point of photoablation is moved inwardly, or away, from the anterior ocular surface.

Care is taken in the operation of Nd:YLF laser 50 not to rupture lens capsule 34 by expansion of laser shock wave. Moreover, if excessive bubbles are formed at the ablation site, as detected, for example, by viewing, with a slit lamp (not shown) the ablation region through cornea 14 and iris opening 26, the laser ablation procedure is discontinued and additional treatment is performed at a later date, for example, in one or two weeks.

By the method described above, the natural lens in an eye can be photoablated by pulsed energy from a laser—preferably an Nd:YLF laser—in a manner correcting myopia, presbyopia and hyperopia and in a manner removing incipient cataracts.

Because the above-described laser-ablative procedures are relatively non-invasive (as compared, for example, to laser photoablation of the cornea to correct vision problems or the surgical removal of a natural lens in the case of cataract) and because lens 18 is non-vascular and contains no nerve supply, no post-ablation inflammation or wound-healing problems are anticipated, and the use of steroids—commonly used after corneal laser photoablation—is not indicated. Moreover, because of its structural nature, lens 18 is not expected to revert—with time—to its pre-ablative shape—as may be the case for laser-ablated corneas.

EXAMPLE

Cataract Induction

Three adult NZA rabbits weighing approximately 3.0–4.0 Kg were anesthetized with 2.0–3.0 cc intramuscular injection of mixture of 5 mg/kg xylazine base (Fermenta Animal Health) and 50 mg/kg ketamine HCL (Aveco, Fort Dodge, Iowa) combined with sterile water. A wire lid speculum was inserted in the interpalpebral fissure of the eye to be operated on.

In one rabbit, a traumatic anterior cortical cataract was produced in the right eye during a corneal wound healing experiment. Briefly, a 2 mm full thickness trephine cut was made in the central cornea with a disposable biopsy punch (Acuderm Inc., Ft. Lauderdale, Fla.). The corneal perforation was sealed with a collagen patch and the anterior capsular tear was sealed by the rabbit's natural fibrin reaction. The anterior cortical cataract remained localized and moved more central in location as newer lens cortical fibers separated the cortical opacity from the anterior capsular scar over time. The anterior cortical opacity remained localized for one year prior to laser treatment.

In two rabbits, a posterior subcapsular cataract was induced by intravitreal injection of 100 $\mu$g Concanavalin A. Rabbits received a 0.1 cc intravitreal injection of Con A at 1 mg/mL (Sigma Chemical Co., St. Louis, Mo.), yielding a total dose of 100 $\mu$g in one eye. Following the injections, rabbits received 1% tropicamide (Alcon, Humacao, Puerto Rico), 10% phenylephrine (Winthrop, New York, N.Y.), and 1% Pred Forte (Allergan, Inc., Irvine, Calif.) four times daily in the test eye for three weeks. Postoperatively, Con A-treated eyes had moderate anterior and posterior uveitis which resolved by three weeks and posterior subcapsular cataracts were noted by three months. The posterior subcapsular opacities remained stable for two months prior to laser treatment.

Focal Laser Photophacoablation

The eye to be operated on was dilated with 1% cyclopentolate (Alcon, Fort Worth, Tex.) and 10% phenylephrine (Winthrop, New York, N.Y.). Animals were anesthetized as mentioned above. A wire lid speculum was inserted to retract the lids, and the eye with the cataract was placed in position at the slit lamp laser.

A Cooper Laser Sonics 4000 Nd:Yag laser with an HeNe aiming beam was used to deliver 697 spots of 2–8.3 millijoules of energy/pulse with a 50 micron spot size to the anterior cortex or nucleus of a normal lens of six NZA rabbits.

An infrared picosecond laser with an HeNe aiming beam (Nd:YLF laser, ISL, San Diego, Calif.) was used to deliver 60–140 microjoules of energy/pulse with a 0.3–0.6 mm$^3$ cube at 1053 nm to one normal lens and three cataractous opacities in three rabbits.

Three different Nd:YLF laser application modes were performed:

(1) Single 20 micron spots with energy between 60–90 microjoules were delivered to different spots in the anterior and posterior part of the opacity of one rabbit. The other normal eye received two 0.3 mm$^2$ monolayer patterns in clear anterior cortex.

(2) At three different locations of another opacity in the second rabbit, a 0.3 mm$^2$ monolayer patter was applied. The monolayer pattern ablates tissue only in a single layer of focus without changing it after this layer has been ablated.

(3) On a third rabbit, multiple cube-like, and therefore three-dimensional, patterns of 1×1×0.2 mm were applied over five different sessions. The energy was set from 90–140 microjoules. The total energy applied with these patterns came to 230–330 millijoules per session with a total number of 150,000–300,000 pulses on each session.

The first rabbit received one treatment. The second rabbit was treated three times and the third rabbit five times. The single treatment consisted of single spots and monolayers whereas all other treatments used three-dimensional patterns.

On all patterns where the depth-movement of the laserfocus had to be taken into consideration, the program of the laser was set so that the plasma would destroy first the deeper parts of the opacity and then work forward to the anterior part. This procedure was chosen in order to bring the plasma away from the delicate posterior capsule as fast as possible.

Description of the Nd:YLF Laser System

As mentioned, the ISL Model 2001 MPL Nd:YLF laser (ISL, San Diego, Calif.) is an infrared laser (1053 nm), operating in the picosecond domain. However, infrared light is not absorbed strongly by the transparent media of the eye. As a consequence, the laser beam is focused to the area where ablation is intended to occur. Areas as small as 1$\mu$ can be ablated by direct microplasma-induction on one hand and by microplasmainduced shock wave on the other hand. The energy necessary to create a plasma in the picosecond domain (60–90 microjoules) is considerably smaller than in the nanosecond domain (1–3 millijoules). As a consequence, the collateral damage to the surrounding tissue is due to the cavitation bubble and the shock wave effect is much smaller. Theoretically, this gives the picosecond laser the capability to operate closer to delicate structure than is possible with the nanosecond laser.

Because of the small amount of tissue ablated by each breakdown, the laser needs to have a high repetition rate of pulses. The ISL 2001 has a repetition rate of 1 kHz (1000 Hz) which gives it the capability of reasonable tissue ablation rates per time unit.

Slit Lamp Biomicroscopy and Photography

Postoperatively, animals were examined daily for one week, weekly for one month, and monthly thereafter by slit lamp biomicroscopy and photography with pupil dilation using 1% Mydiacyl (Alcon Laboratories, Fort Worth, Tex.).

Results

Nd:Yag Laser

Initially, at the time of laser treatment, single 50 micron spot laser pulses of 2–8.3 millijoules/pulse produced gaseous bubble formation in the normal lens which resolved within 24 hours. At one day postoperatively, small ring-like opacities were noted in the area of the original laser spot treatment. in some areas, a faint halo/haze was noted to surround the ring opacity. The halo was noted to be more prominent in the superficial anterior cortex and the nucleus, absent in the deeper cortical regions and tended to fade by 3 months. The pinpoint opacities remained throughout the one year follow-up time.

Nd:YLF Laser

Initially, at the time of laser treatment, single 20 micron spot laser pulses at 60–70 microjoules produced no noticeable effect in the normal lens. With single pulses at 90 microjoules, minute circles were noted in the normal lens only by retroillumination. With a 0.3 mm² rectangle at 90 microjoules, gaseous bubble formation was noted with each laser pulse in the normal lens. A total of two rectangular patterns were directed at the normal lens. After dissolution of the bubbles, the normal clear lens showed an area of expanding empty space at 24–48 hours which resolved by day three and remained normal for the six-month follow-up period.

Similarly, with a 0.3 mm² rectangle at 90 microjoules, gaseous bubble formation was noted with each laser pulse in the anterior cortical opacity in the opposite lens. A total of 43 spots was directed at the inferior aspect of the anterior cortical opacity and the posterior subcapsular opacities of two other eyes. The entire lesion of the cataractous lenses was not treated because of increasing difficulty in focusing the laser beam through the preexisting corneal opacity and bubble formation.

Most of the bubbles reabsorbed within 12 hours. On one rabbit, bubbles persisted for several days after the fifth treatment session. The exact composition of these bubble-like structures can only be determined by histology. At the immediate impact of the laser, two types of bubble formation were noted. One type of bubble occurred during laser firing and collapsed immediately after the laser stopped. Although the exact origin of this effect is unknown, it can be assumed that it was a cavitation-bubble phenomenon. The second type of bubble occurred and expanded slowly and disappeared usually within 12 hours.

The anterior cortical and posterior subcapsular opacities appeared less dense and stabilized by 48 hours. After repetitive treatment, the lens opacities gained additional transparency but the beneficial effects decreased slightly after the third treatment. The area of direct laser treatment appeared to be clearer while the lens opacities appeared to thin and expand as if the lenticular fibers were contracting peripherally. However, there was no evidence of any increase in opacification in any of the treated eyes.

During the fourth treatment of one PSC opacity, the plasma was directed too close to the posterior capsule. This resulted in a micro capsule rupture visible only on electron microscopy and a strong local vitreous reaction with anterior vitreous cells. These effects stabilized after 48 hours and did not change after the fifth treatment.

Throughout the study, there was no evidence of external or anterior chamber inflammation. For that reason, no topical antibiotics or steroid therapy was considered necessary.

As hereinabove noted, the ocular lens is a unique organ in its derivation from one cell type, retention throughout life of all cells that are ever produced, in having no blood or nerve supply and in synthesizing unique proteins. Thus, inflammatory process do not occur and trauma or insult generally results in passive and degenerative changes in the lens with consequent opacification.

The present example shows that focal laser ablation of the normal lens with the Nd:YLF laser selectively removed a part of the lens while retaining its structure and function, and without resulting in irreversible damage/opacification.

However, there are certain conditions where cataract may be reversed, arrested and perhaps ablated. These include the reversibility of galactosemic cataract by a lactose-free diet, the arrest of miotic cataract produced by anticholineserases by cessation of drug therapy, and the arrest of traumatic cataract by sealing of the capsular perforation.

In the present example, a traumatic anterior cortical cataract was followed for one year without evidence of progression. After laser ablation, this opacity showed partial clearing and this suggests that such lesions may be amenable to removal without the necessity for invasive surgical intervention. Similarly, the posterior subcapsular cataracts were stable prior to laser therapy and showed some clearing (although less effect due to difficulty in focusing the energy to the back of the lens). In both cases no damage to the surrounding lenticular tissue or progression of opacification was noted. However, lens capsular scars were not treated and may still present a barrier to good vision.

Although there has been hereinabove described methods for laser photoablation of a natural lens for correcting vision problems for the purpose of illustrating the manner in which the present invention can be used to advantage, it should be understood that the invention is not limited thereto. Therefore, any and all modifications, variations, or equivalent arrangements which may occur to those skilled in the art, should be considered to be within the scope and spirit of the present invention as defined in the appended claims.

What is claimed is:

1. A method for selective removal of ocular lens tissue, for the correction of vision defects, said method consisting essentially of the steps of:

focusing a laser into an ocular lens with a focal point below an anterior surface of the ocular lens where ablation is intended to occur;

pulsing said laser at said focal point; and moving the laser focal point towards the ocular lens anterior surface and pulsing said laser at a selected volume of ocular lens, where ablation is intended to occur, said selected volume being of a size enabling resolve by adjacent healthy ocular lens tissue.

2. The method as claimed in claim 1, where the step of pulsing said laser beam includes pulsing the laser beam at a repetition rate of about 1000 Hertz and a pulse width of about 60 picoseconds.

3. The method as claimed in claim 1 wherein the step of pulsing said laser beam includes pulsing the laser beam with an energy per pulse of between about 1 nanojoule and about 50 millijoules.

4. The method as claimed in claim 1, wherein the step of pulsing said laser beam includes pulsing the laser beam with an energy per pulse of about 3.0 microjoules.

5. The method as claimed in claim 1, including the step of controlling the pulse laser beam to provide at said selected volume of ocular lens to be ablated a beam spot diameter of between about 1 micron and about 20 microns and a zone of effect of less than about 200 microns.

6. The method as claimed in claim 1, including the step of controlling the pulsed laser beam to provide at said selected volume of ocular lens to be ablated a beam spot diameter of about 20 microns and a zone of effect of less than about 50 microns.

7. The method according to claim 1 wherein the focal point moved in a pattern of a plurality of selected volumes in said ocular lens.

8. The method as claimed in claim 1 wherein the selected volume has a cross-section of up to about 0.3 square millimeters.

9. A method of increasing an accommodation amplitude of an ocular lens within a lens capsule of an eye, said method comprising the steps of:

establishing a desired accommodation amplitude for an ocular lens to be treated;

measuring an actual accommodation amplitude for said ocular lens to be treated;

calculating a volume of lens tissue to be removed by subtracting said desired accommodation amplitude from said lens actual accommodation amplitude, said volume of lens tissue being of a size enabling resolve by adjacent healthy ocular lens tissue; and directing a laser at said calculated amount of lens tissue to be removed through the cornea and open iris of said eye, at a nucleus and centrally located older fibers of said ocular lens and into a cortex region thereof without causing substantial photoablation damage to surrounding tissue regions, including the lens capsule, and thereafter directing the laser towards less centrally located fibers of said ocular lens.

10. The method as claimed in claim 9, further comprising the step of using the beam of an aiming laser to direct the pulsed laser beam at said ocular lens.

11. The method as claimed in claim 9, wherein the step of directing a laser includes operating the laser so that the pulses have a pulse width of between about 1 femtosecond and about 1 millisecond.

12. The method as claimed in claim 9, wherein the step of directing a laser includes selecting the laser as an Nd:YLF laser having a wavelength of about 1053 nanometers.

13. The method as claimed in claim 9, wherein the step of directing a laser includes pulsing the laser at a repetition rate of about 1000 pulses per second and operating the laser so that the pulse width is about 60 picoseconds.

14. The method as claimed in claim 9, including the step of controlling the laser so that the spot diameter of the laser beam at the region of the ocular lens to be photoablated is less than about 20 microns.

15. The method as claimed in claim 9, wherein the step of controlling the laser to control the beam diameter includes controlling the laser so that the diameter of a zone of effect of the laser beam at the region of the ocular lens to be removed is less than about 100 microns.

16. The method as claimed in claim 9 including the step of targeting the region of the ocular lens to be removed by impinging a target laser beam on said region by using a targeting laser.

17. The method as claimed in claim 16 wherein said targeting step includes selecting the targeting laser as an HeNe laser.

18. A method for the selective removal of ocular lens tissue of an eye for the removal of incipient cataract, said method consisting essentially of the steps of:

selecting a volume of the ocular lens tissue within a lens capsule to be removed so as to remove incipient cataract, said volume being of a size enabling resolve by adjacent healthy ocular lens tissue;

measuring the incipient cataract and calculating the amount of lens tissue to be removed from said selected volume so as to remove said incipient cataract;

directing an infrared laser beam from the exterior of the eye, through the cornea and open iris thereof, at a point in said selected ocular lens tissue volume at an anterior surface of the ocular lens;

pulsing said laser beam at a frequency between about 1 and about 1000 Hertz and a pulse width of between about 1 femtosecond and about 1 millisecond;

directing the infrared laser at points in said selected ocular tissue volume interior to the ocular lens anterior surface;

adjusting the energy level of said pulsed laser beam so that the beam provides an amount of per-pulse energy without causing substantial shock wave damage to lens tissue, including the lens capsule, surrounding said region; and allowing the selected amount of ocular tissue to be absorbed by healthy tissue adjacent the ocular lens anterior surface.

19. A method for the selective removal of ocular lens tissue of a human eye for the correction of vision defects, including myopia, hyperopia, or presbyopia, said method comprising the steps of:

measuring the physical parameters of said ocular lens tissue shape in order to characterize said vision defect;

selecting a region of the ocular lens tissue within a lens capsule of an eye to be removed in order to correct said vision defect;

calculating from said measured physical parameters a selected amount of lens tissue to be removed from said selected region, the selected amount being a volume of lens tissue necessary to correct said vision defect;

directing an infrared laser beam from the exterior of said eye through the cornea and iris opening thereof and at a point in said selected ocular lens tissue region below an anterior surface of the ocular lens; and pulsing said laser beam at a frequency of between about 1 and about 1000 pulses a second, at a pulse width of between about 1 femtosecond and about 1 millisecond and with an amount of per-pulse energy without causing substantial shock wave damage to lens tissue, including the lens capsule, surrounding said region, said selected region being of a size enabling resolve by adjacent healthy ocular lens tissue.

20. The method according to claim 9 wherein the laser is directed in a pattern to create a plurality of selected amounts in said ocular lens.

21. The method as claimed in claim 10 wherein the step of directing the laser beam includes directing the laser beam Nd:YLF laser having an operating wavelength of at the selected amount of lens tissue with a cross-section of up to about 0.3 square millimeters.

22. The method as claimed in claim 20 wherein the step of pulsing a laser beam includes pulsing the laser beam at a repetition rate of about 1000 Hertz and a pulse width of about 60 picoseconds.

23. The method as claimed in claim 20 wherein the step of pulsing said laser beam includes pulsing the laser beam with an energy per pulse of between about 1 nanojoule and about 50 millijoules.

24. The method as claimed in claim 20 wherein the step of pulsing said laser beam includes pulsing the laser beam with an energy per pulse of about 30 microjoules.

25. The method as claimed in claim 20 including the step of controlling the pulsed laser beam to provide at said region of ocular tissue to be removed a beam spot diameter of between about 1 micron and about 20 microns and a zone of effect of less than about 200 microns.

26. The method as claimed in claim 20 including the step of controlling the pulsed laser beam to provide at said region of ocular tissue to be removed a beam spot diameter of about 20 microns and a zone of effect of less than about 50 microns.

* * * * *